United States Patent [19]

Niemi

[11] 4,293,757
[45] Oct. 6, 1981

[54] AUTOMATIC WELDER'S HELMET HAVING VENTILATION MEANS

[76] Inventor: Francis J. Niemi, 3933 W. Ellis Ave., Chicago, Ill. 60653

[21] Appl. No.: 76,409

[22] Filed: Sep. 17, 1979

[51] Int. Cl.³ .......................... B23K 9/32; A61F 9/06; F16P 1/06
[52] U.S. Cl. ............................................ 219/147; 2/8
[58] Field of Search ................................ 2/8; 219/147

[56] References Cited

U.S. PATENT DOCUMENTS

| | | | |
|---|---|---|---|
| 1,999,639 | 4/1935 | Rosenberger | 2/8 X |
| 2,402,820 | 6/1946 | Kitchen | 2/8 X |
| 3,692,974 | 9/1972 | Thomason et al. | 219/147 |
| 3,838,247 | 9/1974 | Finger et al. | 219/147 |

Primary Examiner—Elliot Goldberg
Assistant Examiner—Keith E. George
Attorney, Agent, or Firm—McCaleb, Lucas & Brugman

[57] ABSTRACT

Improved automatic welder's helmet having pneumatic control to effect closing of the helmet's dark eye shield prior to energizing the electrode for striking the welding arc, and further to maintain the dark eye shield closed until after the arc and weldment's white afterglow have ceased. Additionally, the helmet includes a ventilation system operable to ventilate the helmet and remove annoying welding fumes and smoke from the interior thereof and about the eye shield in its lowered position on the operator's head. In a modified embodiment, the helmet ventilation system operates only when the operator is depressing the electrode holder's control button.

5 Claims, 8 Drawing Figures

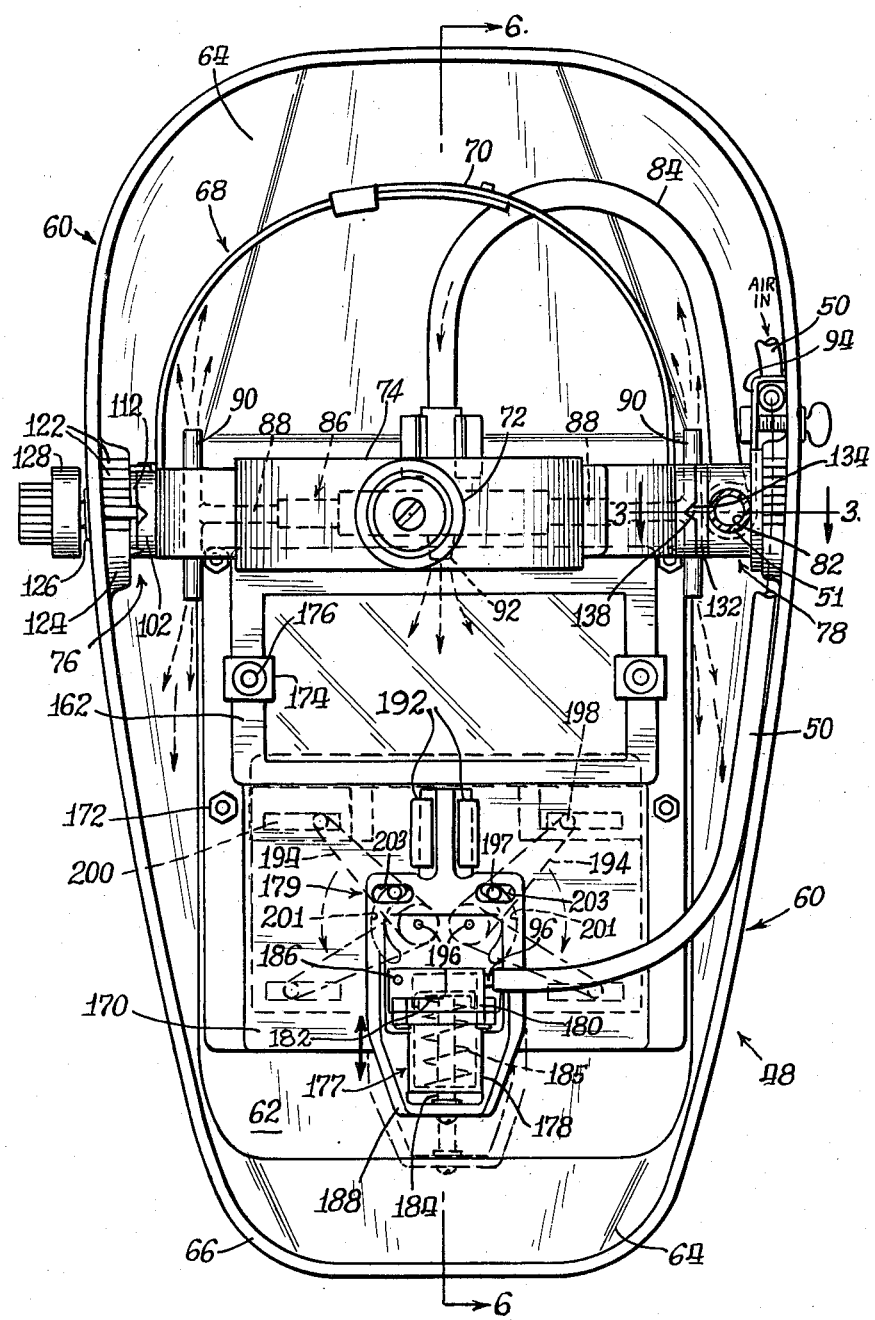
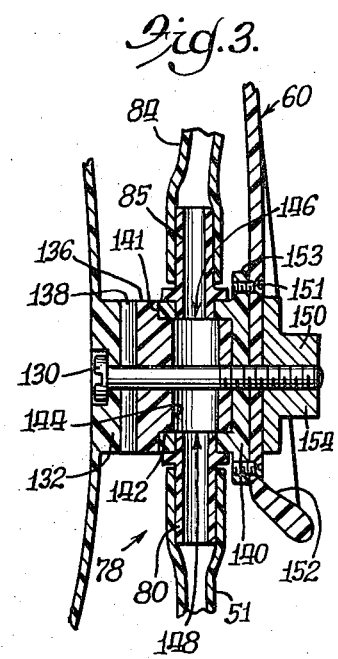
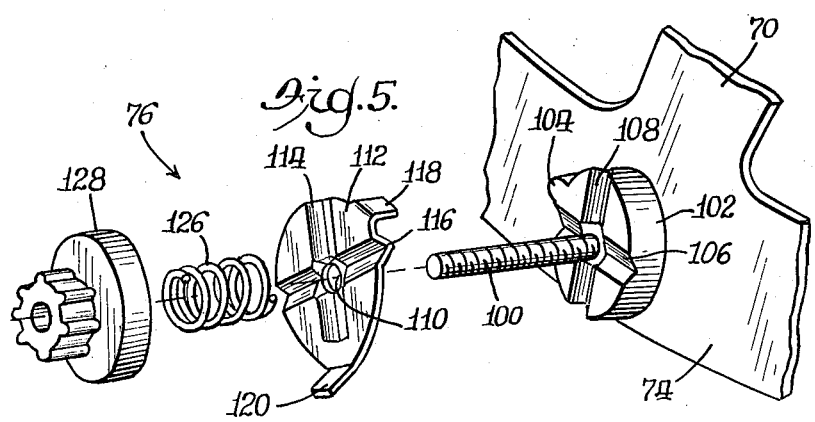
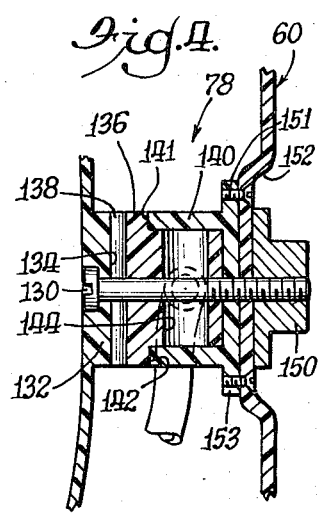

AUTOMATIC WELDER'S HELMET HAVING VENTILATION MEANS

BACKGROUND OF THE INVENTION

1. Field of the Invention

This invention relates to welding helmets and controls therefor, and specifically to welding helmets having automatically controlled eye shields. More particularly, this invention relates to a welder's helmet in which a dark eye shield is moved automatically into position relative to the welder's mask to protect the welder's eyes against injury from the intense flash of a welding arc and which embodies means for ventilating the helmet interior and to clear the eye shield of smoke and fumes.

2. Description of the Prior Art

There have been various attempts in the past to provide an automatic welder's helmet to protect the operator's eyes from the intense welding arc during the welding cycle. As is well known, the intense flash caused by electric arc welding, heli-arc welding, and tack welding and the like, for example, is injurious to the welder's eyes. The typical welder's helmet utilizes a nearly opaque or light radiation absorbing eye piece to block the intense arc light. In some instances, the dark eye piece is permanently affixed to the welder's helmet such that the operator must continuously manually raise and lower his helmet to visually inspect his work. In other cases, the operator can either manually flip up, slide up vertically, rotate out radially, or otherwise move the eye piece to see his work.

One such prior art attempt is U.S. Pat. No. 3,096,430, issued July 2, 1963, which discloses a pneumatically operated eye shield control unit in which the associated electrical circuitry utilizes a time delay relay to assure that the welding arc cannot be struck until the dark eye shield is closed. However, no provision is made for assuring the arc has completely ceased before the dark lens is lowered. Another prior art teaching, typifying prior attempts at automatic welder helmets, is found in U.S. Pat. No. 2,761,046, issued Aug. 28, 1956. This patent discloses a rotary solenoid-controlled mechanism for operating the dark eye shield. The circuitry disclosed in that reference assures that the electrical arc is completed and broken before the shield will re-open. Other prior art devices utilized "Bowden" type wire cable devices to control the dark lens, or a single arm control lever.

A major problem with these and other prior art attempts at automatic welder's helmets has been the presence of cumbersome mechanical linkages and lens mounting frames positioned on the exterior of the face mask of the helmet. These devices required that the helmet, when removed from the operator's head, had to be carefully laid down in only certain positions so as to prevent damage and misadjustment to the lens control. Such exteriorly-mounted components also made for an awkward balance of the helmet when worn.

Another problem with the "Bowden" wire or single control arm type prior art devices is that they tend to bind up in use thereby not allowing the dark lens to close and causing possible eye injury.

Another problem with the previously known automatic welder's helmets is that they often allowed the protective eye shield to be unintentionally opened when the electric arc—which typically completed the circuit controlling the eye shield actuating system—was prematurely broken or otherwise ceased.

Additionally, there has been a continual problem of buildup of unwanted heat and toxic welding fumes within the welder's helmet during long periods of welding, especially when working on pre-heated fabrications. Also there is a need to protect those welders that are sometimes careless and do not properly utilize their helmet, whether of the automatic type or not. There has not been a satisfactory solution to date to overcome these various problems.

The present automatic welder's helmet invention overcomes the foregoing and other problems inherent in the prior art by utilizing the welding torch or electrode holder's control or switch to initiate time-delay relay means which in turn actuates the pneumatic control mechanism closing the helmet's dark eye shield before the arc is energized. A dual lever closing mechanism is used to prevent accidental binding of the dark shield when being closed. Additionally, even if for some reason the welding arc is broken while the operator continues to press the control switch or button, or there is a pressurized air failure, the dark eye lens will automatically close or remain closed thereby assuring protection of the welder's eyes. After the desired welding operation is completed, additional time-delay relay means assures that sufficient time has been expired for the weldment's white afterglow to die off before the pneumatic control mechanism lowers the dark eye shield. This then allows the welder to inspect his work through the clear lens without the need to raise his helmet. Moreover, the compressed air system used to operate the pneumatic eye shield control mechanism is routed through novel means within the welder's helmet to continuously ventilate the helmet during the welding operation. This helmet ventilation feature is used to cool off the welder's head area, to eliminate any foul or toxic welding fumes from the helmet's interior, and, if heated air is used, to prevent moisture from fogging up the helmet's protective lens.

It will be seen that the automatic welder's helmet of the present invention provides increased protection to the welder's eyes; helps to ventilate, cool, and defog the helmet's interior and lenses; and increases welder productivity by eliminating welder down time. The latter occurs because the continuous manual raising and lowering of the welder's helmet or moveable dark lens to visually inspect the work, as required in the prior art devices, is eliminated by the present invention. The present helmet further tends to discourage careless welders from manually holding their helmets up adjacent their faces during short term welding sequences, rather than physically wearing the helmets.

It is therefore an important object of the present invention to provide an automatic welder's helmet having a pneumatic dark eye shield control mechanism to prevent injury to the welder's eyes before, during, and after the welding operation.

It is another object of the present invention to provide an automatic welder's helmet with interior ventilation means for eliminating annoying odors and providing a fresh air supply.

It is yet another object of the present invention to provide a ventilation system for an automatic welder's helmet which may be operated by the raising and lowering of the helmet upon the operator's head, or in response to initiation and termination of the welding cycle.

It is a further object of the present invention to provide electrical and pneumatic control circuitry for an automatic welder's helmet in which there is a time delay between when the dark eye shield is closed and the arc is struck, and a second time delay between when the arc is terminated and the dark eye shield is opened.

It is a still further object to provide control circuitry for an automatic welder's helmet that renders the use of the helmet and an associated welding instrument substantially foolproof.

It is yet a further object to provide a welder's helmet with an automatic dark lens control and ventilating system that is light in weight and can be unobtrusively mounted in the interior of the helmet.

Another object of the invention is to provide an automatic dark shield control system that will automatically close, or remain closed, in the event of a compressed air or electric failure.

The means by which the foregoing and other objects of the present invention are accomplished and the manner of their accomplishment will be readily understood from the following specification upon reference to the accompanying drawings, in which:

FIG. 2 is a rear elevation view of the automatic welder's helmet of the present invention, with some parts broken away for better viewing;

FIG. 3 is an enlarged sectional view of a valve component of the ventilation system of the helmet of FIG. 2, taken along the line 3—3 thereof;

FIG. 4 is an enlarged sectional view of the valve component of FIG. 2, similar to FIG. 3, but depicting its components when the helmet is in a different operating position;

FIG. 5 is an exploded perspective view of a harness pivot component of the helmet of FIG. 2;

DESCRIPTION OF THE PREFERRED EMBODIMENT

Figure 1:
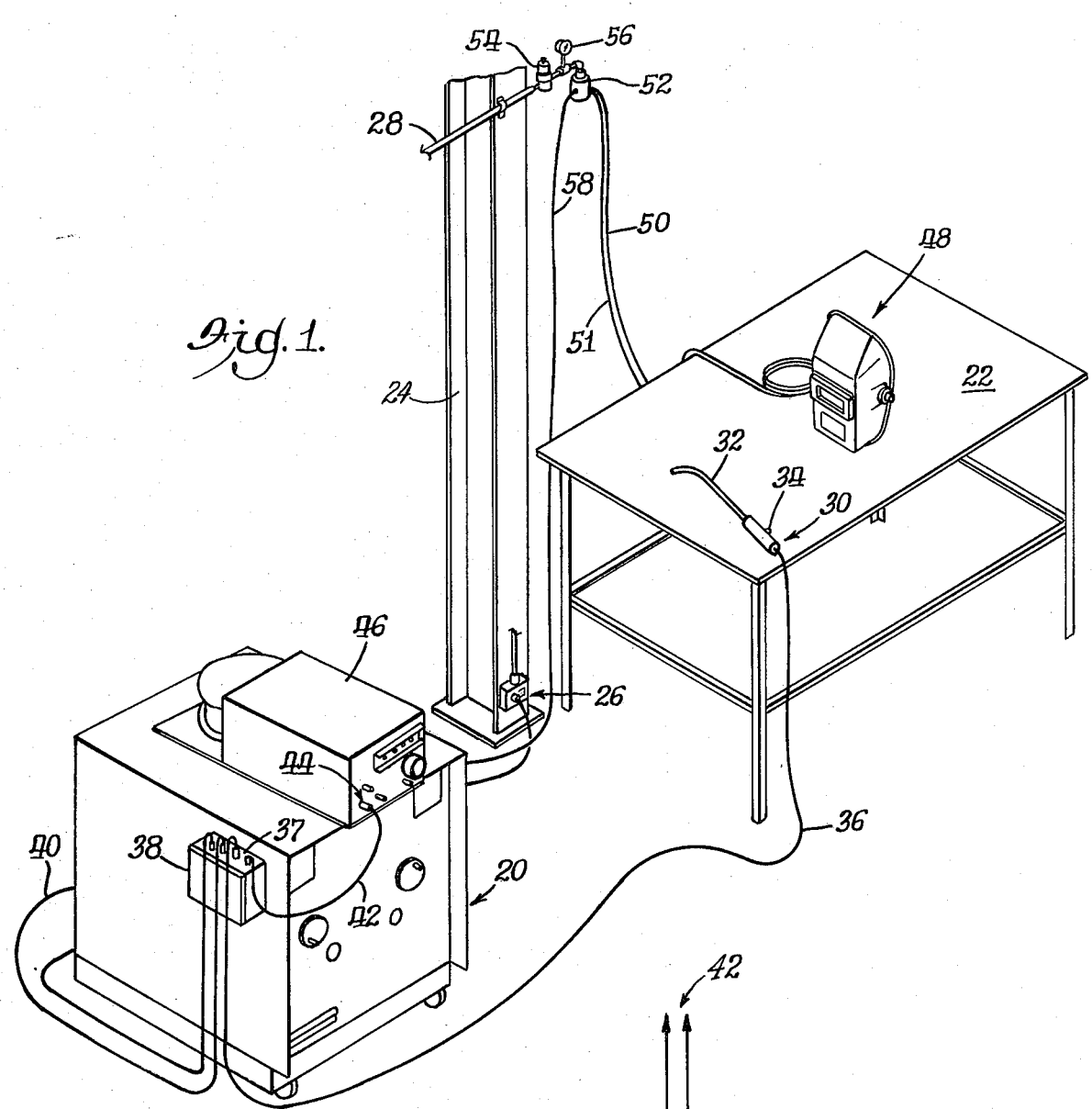
FIG. 1 is a perspective view of a typical welding station wherein the present invention can be utilized, and depicting the various components thereof.

Having reference to the drawings, wherein like reference numerals indicate corresponding elements, FIG. 1 illustrates a typical operating environment for an arc-welding station in which the present invention can be utilized. The welding station includes an electric arc welding machine 20, a work table 22, and a building column or support member 24 carrying a 115-volt A.C. electrical supply 26 and a plant air supply line 28. A well-known welder electrode holder 30 carrying an electrode 32 and having a trigger button or control switch 34 is connected by electrical cord 36 to a receptacle panel 37 of an automatic welder's helmet control box 38; the latter being mounted in a convenient location on the exterior of welding machine 20. The control box 38 is energized over electrical line 40 connected to the 115-volt source 26. The control box 38 is also connected by an electrical line 42 to the remote-switch receptacle 44 of a usual control module 46 for the welding machine 20.

An automatic welder's helmet of this invention, generally referred to by reference numeral 48, is connected by dual air hoses 50, 51 to a solenoid air operated control valve 52. In the preferred embodiment, the smaller diameter air hose 60 typically is a $\frac{1}{4}''$ O.D. plastic hose, while the larger air hose 51 is a $\frac{3}{8}''$ O.D. plastic hose. The solenoid air valve 52 is connected to the plant air supply line 28 through a combination air pressure regulator and line filter device 54 and an optional air pressure gauge 56. The valve 52 is energized via electrical line 58 connected to the welder's helmet control box 38. Preferably, the plant air supply line 28 should supply compressed air regulated to about 20 psi. Additional final filters can be used as desired (see FIG. 7).

Figure 6:
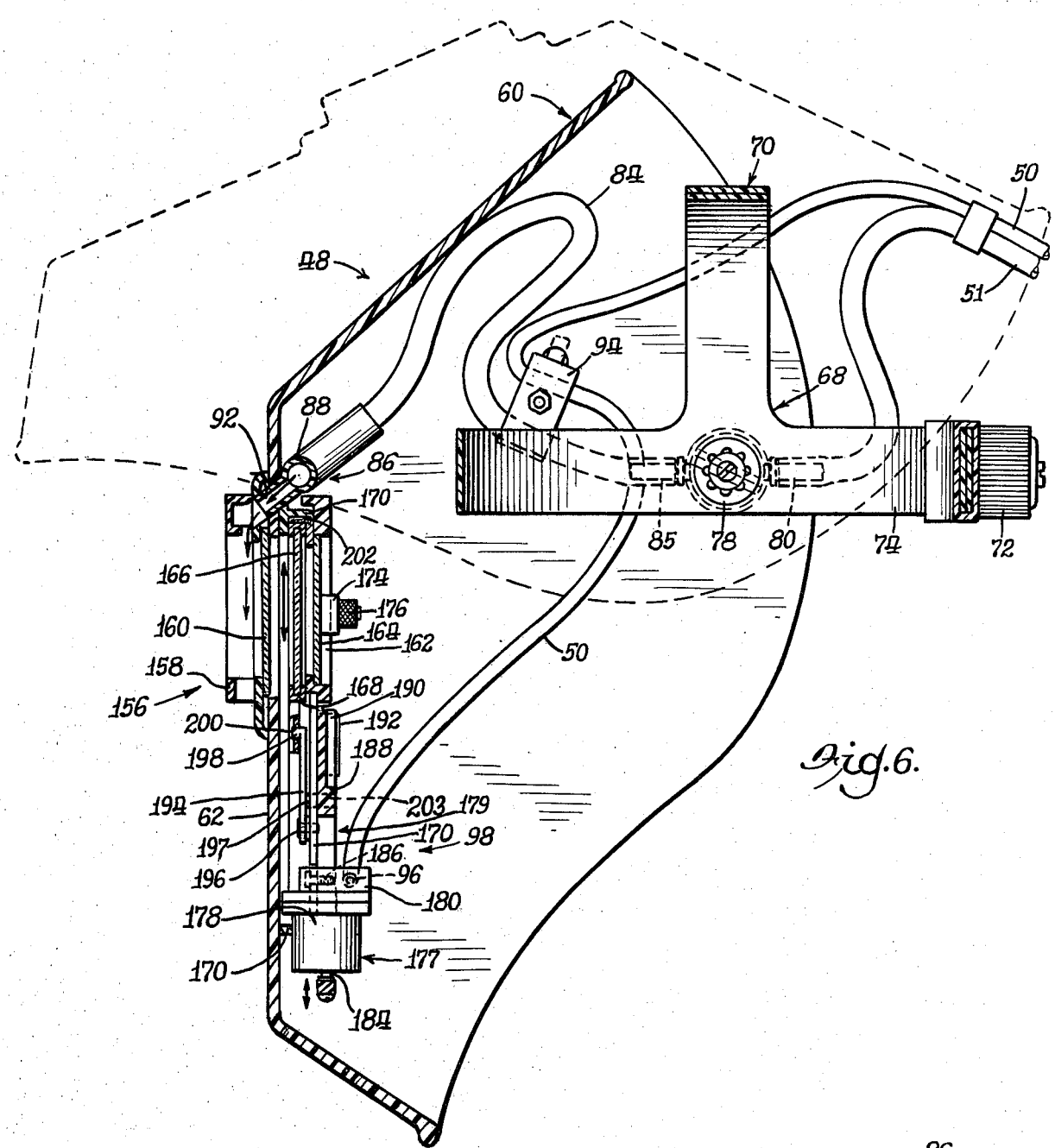
FIG. 6 is a side sectional view of the welder's helmet of FIG. 2, taken along the line 6—6 thereof.

As best seen in FIGS. 2 and 6, the automatic welder's helmet 48 comprises the usual fiberglass hood or plastic headshield 60 having a front planar section 62 and a peripheral or wraparound portion 64; the latter terminating in a beaded edge 66. The helmet 48 utilizes a well-known headband harness 68 having an incrementally adjustable vertical section 70 and an indexing knob 72 for adjusting a horizontal harness section 74, all in a well-known fashion.

The headshield 60 is pivotally mounted to the headband harness 68 by specially configured pivot means, the latter denoted generally as a pivot assembly 76 (left side of FIG. 2) and a combination valve and pivot assembly 78 (right side of FIG. 2), both of which are explained in greater detail later herein. It will be noted (see FIGS. 2, 3 & 6) that the larger air hose 51 is connected through an adapter 80 to an inlet port 82 of the combination valve and pivot assembly 78. A large diameter air feed line 84 then connects the other side of the assembly 78 through a connector 85 to an interior air distribution assembly 86, the latter comprising feed tubes 88 which terminate in vertically-aligned exhaust tubes 90 adjacent each side of the helmet. The air distribution or helmet ventilation assembly 86 also has a front exhaust port 92 (FIG. 6), the purpose of which is explained later herein. A manually adjustable hose clamp and bracket assembly 94 both securely affixes ventilating air feed line 84 and the smaller air hose 50 to the interior surface of headshield portion 64 and can adjustably clamp or regulate air flow through hose 50. The small air hose 50 leads into an inlet port 96 of a pneumatic eye shield control mechanism, generally denoted by reference numeral 98.

As best seen in FIGS. 2 and 5, the harness pivot assembly 76 comprises a threaded fastener element 100 having its head portion (not shown) bearing against the inside of the juncture of harness sections 70 and 74 adjacent a specially configured boss section 102 formed integrally with the harness at that point. The boss 102 carries a radially extending stop portion 104 and two V-shaped detent channels 106, 108 formed at right angles to one another. The fastener 100 is inserted through a central opening 110 in a pivot plate 112 which carries two detent notches 114, 116. The latter are formed to correspond respectively to detent channels 106 and 108 on boss 102. An inwardly extending dog member 118 is formed on plate 112 and is operable to engage stop 104 of boss 102. Similarly, an outwardly extending dog member 120 is formed on plate 112 to engage any of a plurality of notches 122 carried on an inwardly extending boss section 124 of helmet portion 64.

Turning to the combination valve and harness pivot assembly or so-called rotary valve 78 (FIGS. 2, 3, and 4), a second threaded fastener 130 extends through a central opening in a second boss section 132 formed similarly to boss 102, but at the other side or juncture (see right side of FIG. 2) of harness portions 70, 74. The boss section 132 carries a V-channel 134. A pivot valve section 136 carrying a detent notch 138 and having a central bore 144 is also rotatably supported by the fastener 130. A stationary valve housing 140 is rigidly mounted to an inwardly extending boss 152 on helmet portion 64 by fasteners 151 extending through the flange 153. The housing 140 has an inner cylindrical end 141 channeled over an annular shoulder 142 formed on pivot valve section 136. The valve housing 140 contains an exhaust air port 146 and inlet air port 148, both capable of being in registry with central bore 144 of valve section 136 under certain operating conditions. The inlet port 148 accepts adapter 80 and air hose 51, while the exhaust port 146 accepts adapter 85 and air feed line 84. Housing 140 is rigidly mounted to an inwardly extending boss 152 on helmet portion 64 by fasteners 151 extending through the flange 153. A threaded hand knob 154 is used to assemble fastener 130 and the various components it supports to headshield 60.

The shutter structure for operating the dark eye shield will now be described, with reference to FIGS. 2 and 6. A three-part eye lens assembly, generally denoted by reference numeral 156, includes an outer lens frame 158, a clear outer lens 160, an inner lens frame 162, and a clear inner lens 164. These clear lenses can be glass, plastic, or other well-known materials and are used to prevent weld splatter and other particles from damaging the dark lens, or injuring the welder's eyes when the dark lens is open. The important third lens or dark glass eye shield 166 is retained within a lens frame 168 which in turn is slideably retained within a lens frame housing 170. The housing 170 is affixed to the interior surface of front portion 62 of headshield 60 by threaded fasteners 172. The inner lens frame 162 is detachably retained to lens frame housing 170 by angle clips 174 and associated threaded fasteners 176.

The pneumatic eye shield control mechanism 98 used to slidably actuate the dark eye shield 166 comprises an air cylinder 177 and a yoke assembly 179. The air cylinder 177 comprises a lower body portion 178, an upper head portion 180 having an inlet air port 96 connected to the small air hose 50, a flexible diaphragm member 182 retained between portions 178 and 180, a piston shaft 184, and an extension spring 185. The latter acts to keep the diaphragm 182 and hence the shaft 184 (and lens 166) in their uppermost positions (see FIG. 2). The air cylinder 177 is affixed to the lower central portion of lens frame housing 170 by threaded fasteners 186. The lower end or yoke 188 of the yoke assembly 179 is centrally joined to the lower end of piston shaft 184. An upwardly extending neck portion 190 of yoke 188 is slidably retained within and between a pair of guides 192 formed on housing 170. A pair of guide arm members 194 are pivotally retained by pins 196 to housing 170. Each arm 194 carries an inwardly turned drive lug 197, and an outwardly turned drive lug 198. The lugs 198 are each slidably retained within rectangularly-shaped drive openings 200 (horizontal in FIG. 2) formed in the lower portion of lens frame 168. Likewise, the lugs 197 are each slidably retained in arcuate-shaped guide openings 201 formed in housing 170 and rectangularly-shaped drive openings 203 formed in the upper portion of yoke 188. A strip of cushioning material 202, fastened across the upper edge portion of lens frame housing 170 acts as a resilient stop to cushion the upward travel of dark shield 166 and lens frame 168.

Figure 7:
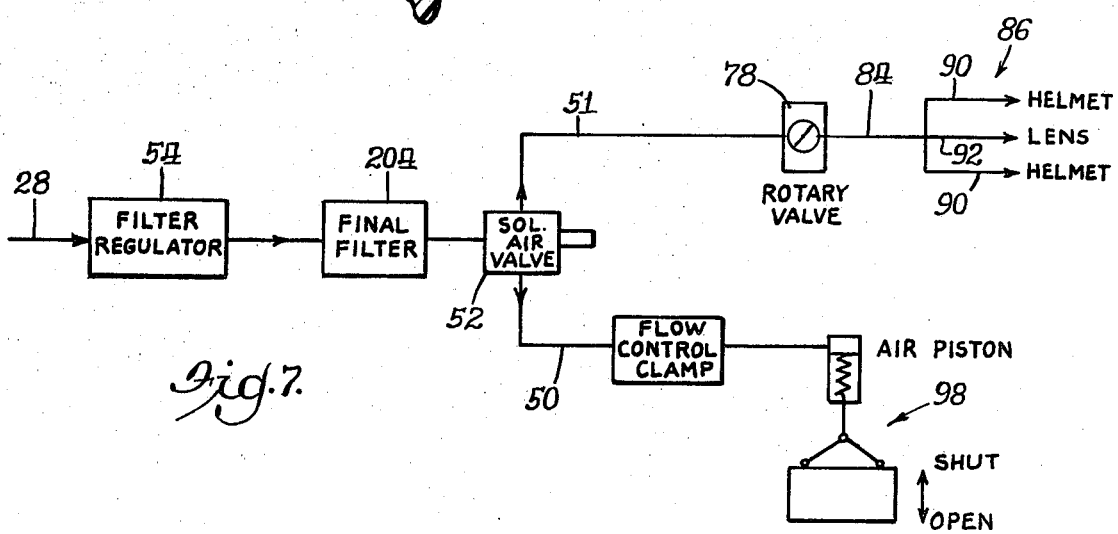
FIG. 7 is a schematic diagram depicting the pneumatic shutter control and ventilation system of the helmet of the present invention.

Schematic diagram FIG. 7 depicts the various components of a preferred embodiment of the pneumatic lens control and ventilation system for the present invention. The pressure of the plant air supply line 28 is regulated by the combination filter-regulator 54 and then filtered through an optional final filter 204 to remove any unwanted carbon monoxide or particulate matter. An optional air heater (not shown) can be added as desired. The filtered and pressure-regulated air is then piped to solenoid air valve 52 where it is capable of being shunted in two directions. One route from solenoid 52 is through large diameter air hose 51 to the air rotary air valve 78 and then on through line 84 to the air distribution assembly 86. At this point the air is distributed to the interior of the helmet 48 via exhaust ports 90 and across the clear outer lens 160 via port 92. The other route from the solenoid 52 is through the small diameter hose 50 and the flow control clamp 94 and on to the inlet port 96 of the pneumatic lens control mechanism 98 for operating the dark eye shield 166. It will be understood that the clamp 94 can be adjusted to regulate the speed of opening lens 166 by adjusting the air pressure to mechanism 98. This also regulates closing speed by restricting line back pressure against which the spring 185 works in the closing operation.

It will be also understood that, in the preferred embodiment just described, the solenoid valve 52 is of the normally-open type and operates to control both the helmet ventilation system and the pneumatic shutter system, i.e., alternately providing compressed air to either air hose 51 or hose 50. This assures supply of air to the helmet only during a welding cycle, but not when the welder has his helmet on and the dark lens is lowered. As explained in more detail later herein, the solenoid valve 52 may also be placed in line only with the pneumatic shutter assembly and not with helmet ventilation system. This would assure constant air flow to the helmet whether the welder is welding or not. This is desired in continuous welding situations or where preheated weldments are being fabricated.

Figure 8:
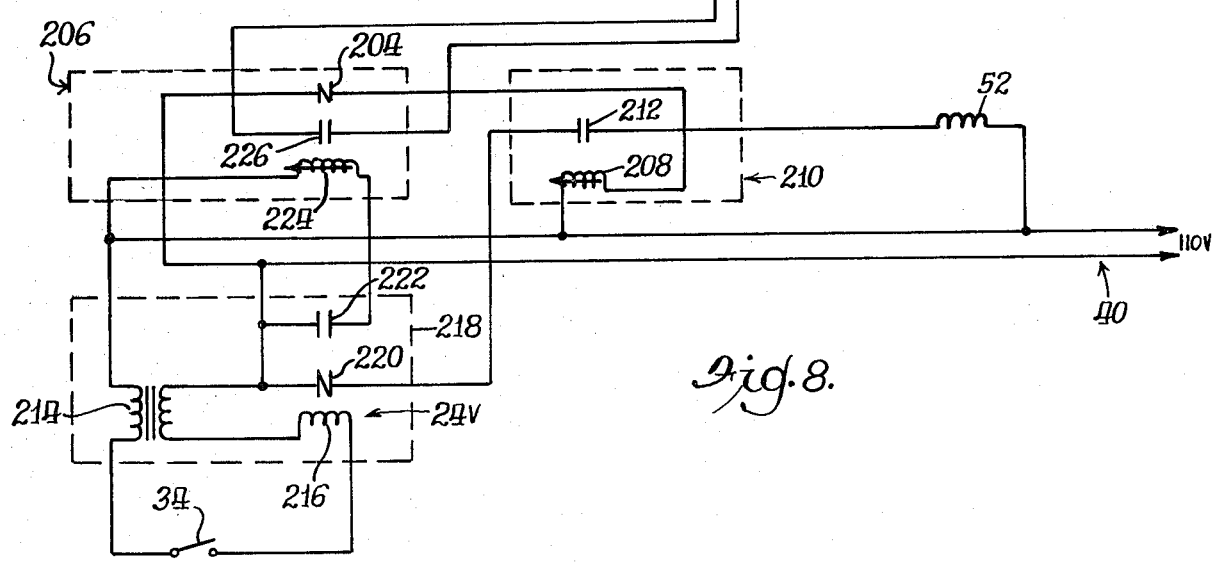
FIG. 8 is a schematic diagram of the electrical control circuitry employed with the helmet of this invention.

Turning now to FIG. 8, there is shown a schematic diagram of the electrical control circuitry for the control box 38 for the herein-disclosed helmet. When the control box is energized, by supplying 110 A.C. power via electrical cord 40, power flows through the normally closed contact 204 of a first time delay relay circuit, generally denoted by reference numeral 206. The power then travels from contact 204 to the variable time delay relay 208 of a second time delay relay circuit, generally denoted by reference numeral 210. After an initial adjustable time delay, from 0.1 to 1 second, for example, the contact 212 closes and the air valve solenoid 52 is energized. This has the effect of placing solenoid 52 in its normal operating condition whereby it supplies regulated compressed air to air cylinder 177. Accordingly, the dark lens is placed in its lowered or open position. This enables the welder to wear the helmet in the lowered position and visually inspect his work through the clear lenses.

When the welder desires to perform a welding operation, he presses trigger switch 34 on electrode holder 30. As seen in FIG. 8, closing switch 34 has the effect of directing power through step down transformer 214 and energizing a 24 volt power relay 216 of a switching relay circuit 218. Upon energization, power relay 216 causes a normally closed contact 220 to open and closes a normally open contact 222. The opening of contact 220 causes the solenoid valve 52 to be de-energized, thereby stopping the flow of compressed air to air cylinder 177. This allows extension spring 185 to automatically raise the dark lens 166 into its closed position. Additionally, the closing of contact 222 allows a variable time delay relay 224 of circuit 206 to begin timing. After a second time interval similar to that of variable relay 208, the normally open contact 226 closes and the normally closed contact 204 opens. Opening of contact 204 has the effect of de-energizing the time delay relay circuit 210, thereby placing it in a ready position for the next cycle. The closing of contact 226 then provides a signal for the first time, via line 42, to the welding machine 20 to initiate the welding cycle.

When the welder has completed his welding cycle, all the time having his dark lens 166 in its closed position to protect his eyes, he releases trigger button 34. This has the effect of de-energizing switching relay circuit 218, returning its contacts 220 and 222 to their normal positions. The opening of normally open contact 222 de-energizes time delay relay circuit 206, thereby terminating the weld signal to control module 46 and stopping the electric arc. Now, power through the normally closed contact 204 energizes the variable relay 208. After a time delay—purposely set to allow the white afterglow of the just-completed weldment to be safely diminished—the normally open contact 212 is closed. This then again allows current to pass through re-closed contact 220 and supply current through the now closed contact 212 again to the solenoid valve 52. This has the effect of again providing compressed air to air cylinder 177 and reopening dark lens 166. For the first time, the welder can now visually inspect his just-completed weld and set up his next weld, all without removing his helmet or even raising it upon his head. This then completes one cycle of operation of the electrical control circuitry of the present invention. It will be understood that the use of time delay relays assure that the lens 166 will not hop up and down, as could occur with the repetitive welds in a heli-arc process such as filling a crater.

Turning now to an operational description of the herein-disclosed welding helmet, it can be seen that a welder can place the automatic welder's helmet 48 upon his head and rotate the head shield 60 into its lowered position. Once the control box 38 is energized, he will be able to visually inspect his welding station as the dark lens 166 will be in its lowered position. As explained in the preferred embodiment, the solenoid valve 52 controls both the air to the ventilation system as well as to the pneumatic shutter assembly. When the operator is not welding, the compressed air is being shunted to the air cylinder 177 thereby moving the dark lens 166 in its lowered position. Thus, the interior of the helmet 48 is not receiving ventilation air. However, when the operator depresses control button 34 and in the-above described electronic control operations occur, it will be seen that the compressed air is then shunted via solenoid valve 52 to the helmet ventilation system. Accordingly, compressed air ceases to flow through small diameter air hose 50 and begins flowing through large air hose 51. Since the headshield 60 is in its lowered position, the rotation of rotary valve 78 has placed bore 144 of valve body 40 into alignment with adaptors 80 and 85 such that compressed air flows through feed line 84 on to air distribution assembly 86. Thus, in the preferred embodiment, when the welder is performing a weld with his helmet lowered, he is receiving internal helmet air ventilation. This includes ventilation across the exterior of outer clear lens 160 (see arrows in FIG. 6). If desired during cold weather, the compressed air could be preheated so that the air flowing across outer lens 160 and that adjacent inner lens 164 on the helmet's interior continuously defoggs those lenses.

In an alternate embodiment (not shown), it will be understood that solenoid valve 52 may be modified such that it only controls air hose 50 and thus air cylinder 177. In such an embodiment, the air line 51 would come directly off plant air supply 28 after the regulator 54 but prior to solenoid valve 52. With that arrangement, there is a constant supply of compressed air to the rotary valve 78. Then the welder would receive a continuous flow of air to the interior of helmet 48. The only time the helmet would not receive air is when he vertically raises the headshield 60 thereby closing rotary valve 78 by placing bore 144 out of registry with air hose 51 and feed line 84. Such a condition helps preserve the plant air supply as where the welder frequently raises his helmet to make repetitive set-ups. In yet another alternate embodiment, the rotary valve 78 could be eliminated altogether to provide continuous ventilation of the helmet.

It will be understood that the presence of extensive spring 185 assures that the dark lens 166 will automatically close or remain closed in case of a compressed air or electrical failure. Also, the trigger switch 34 can be modified to be in the form of a footswitch (not shown) or the control switch for a heli-arc, metallic-arc, gas, wire feed and other known types of welding processes with which the present invention is fully adaptable.

From the foregoing, it is believed that those skilled in the art will readily appreciate the unique features and advantages of the present invention over previous types of automatic welder helmets. Further, it is to be understood that while the present invention has been described in relation to particular preferred and alternate embodiments as set forth in the accompanying drawings and as above described, the same nevertheless is susceptible to change, variation and substitution of equivalents without departure from the spirit and scope of this invention. It is therefore intended that the present invention be unrestricted by the foregoing description and drawings, except as may appear in the following appended claims.

The embodiments of the present invention in which an exclusive property or privilege is claimed are defined as follows:

1. In an automatic welder's helmet for use with a welding machine, the combination comprising: an open back headshield, head harness means pivotally connected to said headshield for supporting the same on the head of an operator, a movable dark eye lens slidably mounted in a frame secured about an opening in said headshield and operable to slide over said opening between open and closed positions, pneumatic operating means protectively mounted within said headshield for opening said dark eye lens, spring means associated with said pneumatic means and operable to effect closing of said dark eye lens; electrical control means for controlling operation of the welding machine and said pneumatic means, said electrical control means including a first time delay means for delaying energization of the welding machine for a period of time until after said dark eye lens has moved to its closed position, and a second time delay means for delaying the movement of said dark lens to its open position for a period of time at least until after the welding cycle has been completed; and helmet ventilation means communicating with the interior of said headshield and operably controlled by said control means to supply fresh air to the interior thereof whenever said lens is in its closed position.

2. The invention of claim 1, including adjustable control means operable to regulate the air supply to said pneumatic means, thereby to enable adjustment of the speed of movement of said dark eye lens.

3. The combination of claim 1, and rotary valve means associated with said head harness and headshield and rotatably responsive to raising and lowering movements of said headshield, said rotary valve means serving to interrupt the flow of ventilation air to said ventilation means whenever said headshield is manually raised.

4. In an automatic welder's helmet of the type having a movable dark lens and control means therefor, the control means being actuated by operating controls for the welding instrument, the improved combination comprising: an open back headshield member, a head harness pivotally connected to said headshield member for supporting the same on the head of an operator, an eye protective dark lens assembly slidably mounted in a frame over an opening in said headshield member and operable to move between closed and opened positions, a pneumatic lens control mechanism mounted protectively within said headshield member and comprising air cylinder means having a piston shaft responsive to movements of said cylinder means, yoke means disposed symmetrically about said cylinder means and connected to said shaft, guide means slidingly supporting said yoke means for reciprocating movements coaxially of said cylinder and shaft, a pair of divergently related rigid guide arms adjacent said yoke means; each being pivotally anchored at one end, means intermediate the ends of each of said arms providing sliding pivotal connection with said yoke means whereby said arms are simultaneously arcuately driven in response to linear reciprocation of said yoke means, slidable connection means joining the outer ends of said arms to opposite lateral margins of the dark lens whereby to linearly reciprocate said lens in response to arcuate movements of said arms, said arms being symmetrically aligned with respect to the central axis of said lens, yoke means and piston shaft whereby to uniformly support and evenly drive said lens in its frame; and electrical control circuitry means responsive to operation of the operating controls to actuate said pneumatic lens control mechanism in a manner to maintain said lens closed for a predetermined time period prior to initiation of a welding cycle and for an additional period after termination of said cycle.

5. A welding helmet for use with an electric arc welding system, comprising: an open back headshield member, a head harness, pivotal means joining said harness to said headshield member whereby to support the latter on the head of an operator and provide for its pivotal movements between raised and lowered positions; helmet ventilation means communicating directly with the interior walls of said headshield member and comprising air distribution means protectively mounted within said headshield member and air supply means located exteriorly thereof; said pivotal means comprising rotary valve means in communication with said air distribution means and said air supply means and operable in response to pivotal movements of said headshield member, whereby when said headshield member is in its lowered position, the air supply means is in direct commuication with said air distribution means and when said headshield member is in its said raised position, said air supply means is isolated from said air distribution means.

* * * * *

UNITED STATES PATENT AND TRADEMARK OFFICE
CERTIFICATE OF CORRECTION

PATENT NO. : 4,293,757

DATED : October 6, 1981

INVENTOR(S) : Francis J. Niemi

It is certified that error appears in the above—identified patent and that said Letters Patent is hereby corrected as shown below:

Column 4, line 5, "60" should be -- 50 --; and

Column 7, line 65, "40" should be -- 140 --.

Signed and Sealed this

Fifteenth Day of December 1981

|SEAL|

Attest:

Attesting Officer

GERALD J. MOSSINGHOFF

Commissioner of Patents and Trademarks